(12) United States Patent
Ryu (10) Patent No.: US 11,583,236 B2
(45) Date of Patent: Feb. 21, 2023

(54) APPARATUS FOR MARKING IRRADIATION AREA FOR HANDHELD X-RAY DEVICE

(71) Applicant: DEXCOWIN Co., Ltd., Seoul (KR)

(72) Inventor: Seung Bum Ryu, Seoul (KR)

(73) Assignee: DEXCOWIN CO., LTD., Seoul (KR)

(*) Notice: Subject to any disclaimer, the term of this patent is extended or adjusted under 35 U.S.C. 154(b) by 163 days.

(21) Appl. No.: 17/329,540

(22) Filed: May 25, 2021

(65) Prior Publication Data

US 2022/0378387 A1    Dec. 1, 2022

(51) Int. Cl.
*A61B 6/08*      (2006.01)
*A61B 6/00*      (2006.01)

(52) U.S. Cl.
CPC .............. *A61B 6/08* (2013.01); *A61B 6/4405* (2013.01); *A61B 2562/166* (2013.01)

(58) Field of Classification Search
CPC ..... A61B 6/4405; A61B 6/547; A61B 1/0684; A61B 2090/376; A61B 2034/2055; A61B 2034/107; A61B 2034/2065; A61B 5/742; A61B 2017/0092; A61B 1/00163
See application file for complete search history.

(56) References Cited

FOREIGN PATENT DOCUMENTS

EP         3311743 A1 *   4/2018  ............. A61B 6/102
KR       10-1404004 B1    6/2014

* cited by examiner

*Primary Examiner* — Don K Wong
(74) *Attorney, Agent, or Firm* — Novick, Kim & Lee PLLC; Jae Youn Kim (57) ABSTRACT

Proposed is an apparatus for marking an irradiation area for a hand-held X-ray device, the device including an upper cover, a lower cover, an X-ray radiation unit, a radiation tube, the apparatus, and a lower support, the apparatus including: a cylindrical member; a reflector; a PCB guide; a PCB; an LED light source; and a fastening screw, wherein light emitted from the LED light source is reflected by the reflector and marks the irradiation area on a subject in front of the reflector.

10 Claims, 7 Drawing Sheets

APPARATUS FOR MARKING IRRADIATION AREA FOR HANDHELD X-RAY DEVICE

BACKGROUND OF THE INVENTION

Field of the Invention

The present disclosure relates to an apparatus for marking an irradiation area for a hand-held X-ray device. More specifically, the present disclosure relates to a technology for an apparatus that simply includes an LED light source inside a radiation tube. Because a hand-held X-ray device has a small internal structure, the apparatus does not employ a complex collimator structure that uses a reflector, a diaphragm, or the like.

Description of the Related Art

Usually, an X-ray beam needs to be aligned in a manner that is incident perpendicularly to a subject and is above the center of a sensor for acquiring an image. When the X-ray beam is not aligned in this manner, a cone-cut phenomenon occurs. A cone-out portion, resulting from being insufficiently exposed to X-rays, appears as a post-processing transparent area in X-ray imaging. When an image is expressed digitally, the cone-out portion appears as being opaque or in white.

Figure 1:
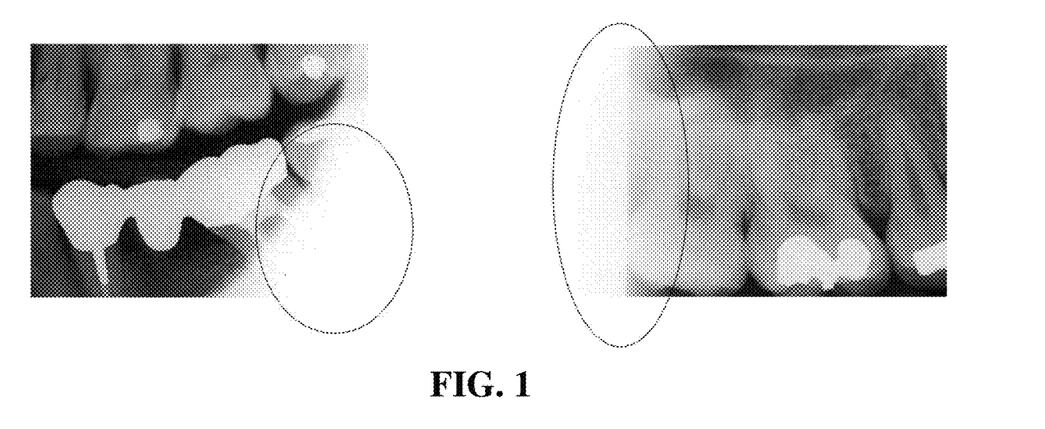
FIG. 1 is a photograph showing a cone-cut phenomenon.

FIG. 1 is a photograph showing the cone-cut phenomenon.

To prevent the cone-out phenomenon, the center of the X-ray beam is aligned in a manner that is perpendicular to an image sensor. Unsuitable fixation of the image sensor also causes the cone-out phenomenon.

While being held by a sensor holder, a sensor for acquiring an image of the subject is inserted into an oral cavity to capture the image thereof. At this point, a user regards the end of the sensor holder as a position of the image sensor in the oral cavity. Then, the user aligns a hand-held X-ray device with a straight line, causes an emission angle to be in the straight line with a subject, and performs X-ray imaging.

Figure 2:
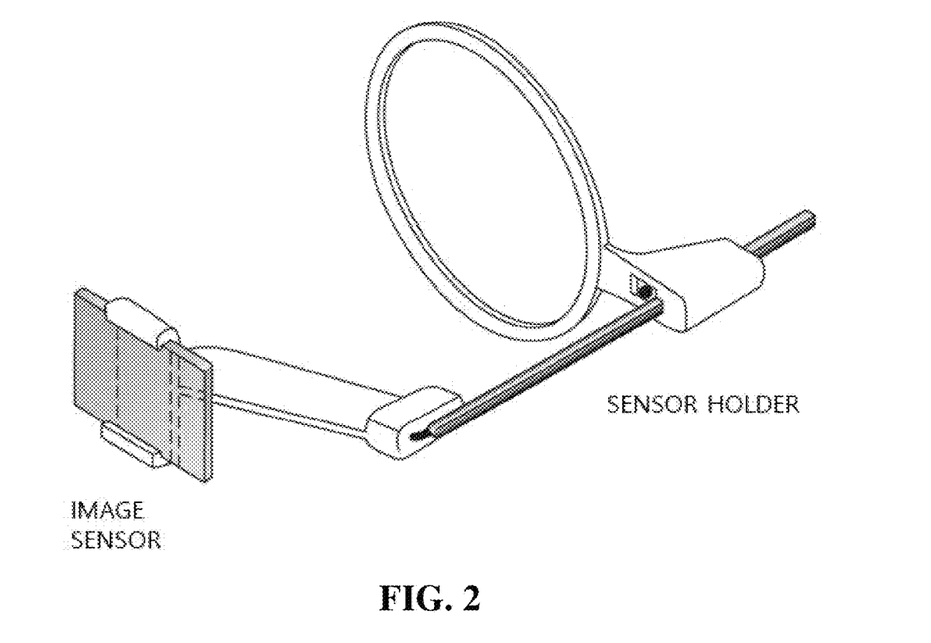
FIG. 2 is a view illustrating a commonly used sensor holder.

FIG. 2 is a view illustrating a commonly used sensor holder;

With reference to FIG. 2, the size and weight of the sensor holder make the sensor holder inconvenient to use. Furthermore, the long distance of the hand-held X-ray device to the subject requires an increase in X-ray radiation time. Thus, long-time X-ray exposure can have a harmful effect on a human body.

In addition, a collimator is difficult to install within a radiation tube of the hand-held X-ray device.

An X-ray collimator itself weighing 2 kg or more in the related art is fairly heavy. A volume of the X-ray collimator also makes the X-ray collimator difficult to mount inside the radiation tube.

The hand-held X-ray device itself weighs 1.5 Kg to 2.5 Kg. An X-ray collimator having a diaphragm in the related art weighs 2 Kg or more. Thus, the addition of the X-ray collimator to the hand-held X-ray device makes the hand-held X-ray device less portable.

A distance of 5 cm or 2 inches from an end portion of the radiation tube of the hand-held X-ray device to the subject is recommended to acquire a high-quality image. However, when a separate large-volume collimator is mounted in the front of the radiation tube, the distance for acquiring the high-quality image cannot be secured.

The foregoing is intended merely to aid in the understanding of the background of the present disclosure, and is not intended to mean that the present disclosure falls within the purview of the related art that is already known to those skilled in the art.

DOCUMENT OF RELATED ART (Patent Document 1) Korean Patent No. 10-1404004 (Jun. 13, 2014)

SUMMARY OF THE INVENTION

According to the present disclosure, there is provided an apparatus capable of marking an X-ray irradiation area for a hand-held X-ray device.

The apparatus according to the present disclosure does not employ a complex collimator structure that uses a reflector, a diaphragm, or the like because the hand-held X-ray device has a small internal structure. Instead, the apparatus includes an LED light source to be simply mounted inside a radiation tube of the hand-held X-ray device and thus can mark the X-ray irradiation area.

The apparatus according to the present disclosure employs a structure where heat occurring in the LED light source is dissipated from the LED light source itself. This structure enhances the portability of the hand-held X-ray device and thus increases the user convenience in use.

The use of the apparatus for marking the irradiation area for the hand-held X-ray device according to the present makes it possible to align an X-ray beam emitted to a subject and an image sensor with each other in an exactly perpendicular manner.

The apparatus for marking the irradiation area for the hand-held X-ray device has a simple lightweight structure enhancing the portability. Thus, the hand-held X-ray device, made portable, can be used conveniently without being fixed to a specific place.

The apparatus for marking the irradiation area for the hand-held X-ray device, itself, employs a structure where the LED light source is cooled. Thus, the efficient heat dissipation and the convenience in use can be provided.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 3:
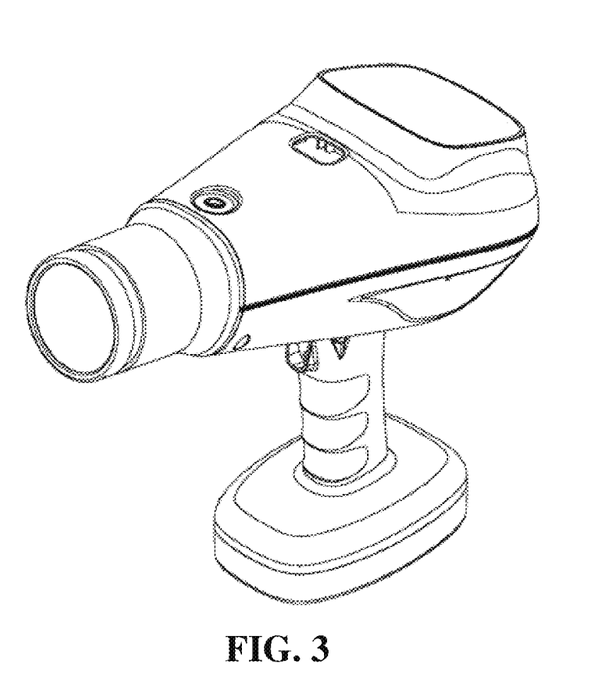
FIG. 3 is a view illustrating a hand-held X-ray device including an apparatus for marking an irradiation area according to an embodiment of the present disclosure.

FIG. 3 is an exterior appearance of a hand-held X-ray device including an apparatus for marking an irradiation area according to an embodiment of the present disclosure.

The hand-held X-ray device can provide simplified portability to a user, compared with a stationary X-ray device. However, when X-ray imaging is performed using a portable hand-held X-ray device, the X-ray beam and a subject are not precisely aligned with each other. Thus, a cone-cut phenomenon or the like occurs frequently.

The X-ray imaging can be performed without causing the cone-cut phenomenon or the like by additionally including a sensor holder for precise alignment. However, the inconvenience of additionally using the sensor holder, the problem in securing a distance to the subject for the X-ray imaging, long-time exposure to X-rays, and the like occur. According to the present disclosure, it is proposed that the apparatus for marking the X-ray irradiation area is provided inside a radiation tube of the hand-held X-ray device in FIG. 3.

Figure 4:
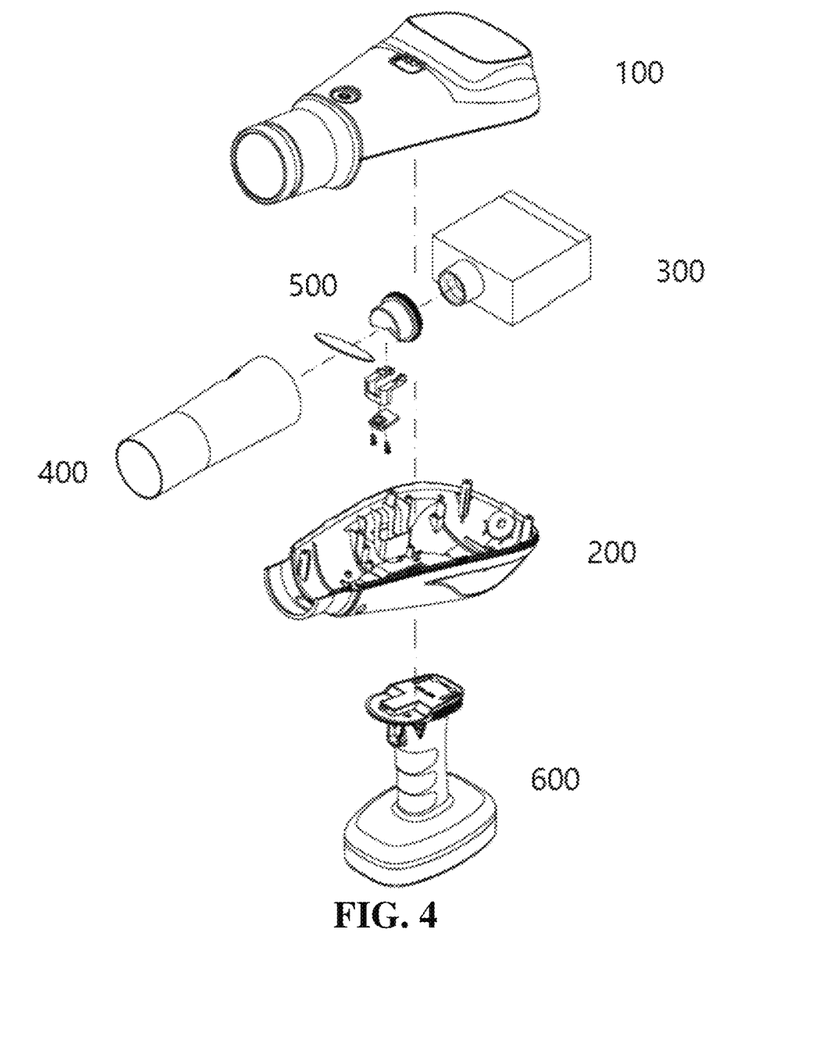
FIG. 4 is a perspective exploded view illustrating the hand-held X-ray device including the apparatus for marking the irradiation area according to the embodiment of the present disclosure.

FIG. 4 is a perspective exploded view illustrating the hand-held X-ray device including the apparatus for marking the irradiation area according to the embodiment of the present disclosure. An apparatus 500 for marking the irradiation area is coupled, in a screw-fastened manner, to a combination member within the radiation tube.

The hand-held X-ray device includes an upper cover 100, a lower cover 200, an X-ray radiation unit 300, a radiation tube 400, the apparatus 500 for marking the irradiation area according to the present disclosure, and a lower support 600.

The hand-held X-ray device includes the apparatus 500 for marking the irradiation area, in the middle of a pathway to the subject. The apparatus 500 for marking the irradiation area in advance marks the irradiation area that guides X-rays, emitted from the X-ray radiation unit 300, toward the subject. Thus, the X-rays pass through the radiation tube 400 and precisely reach the subject.

An LED light source is included in the apparatus 500 for marking the irradiation area. When the LED light source is operated before the X-rays are emitted, light emitted from the LED light source in advance marks the irradiation area to be irradiated with the X-rays passing through the radiation tube 400, on the subject.

The irradiation area marked on the subject by the light emitted by the LED light source can be viewed in advance. Thus, while viewing the irradiation area, it can be checked whether or not the irradiation area is exactly the same as an area, on which the X-Ray imaging is required, of the subject. If not, a fine adjustment can be made for exact positioning of the irradiation area. If the irradiation area to be irradiated with the X-rays is exactly the same as the area, on which the X-ray imaging is required, of the subject, the X-ray radiation unit 300 emits the X-rays and thus performs the X-ray imaging.

Desirably, the LED light source and the X-ray radiation unit 300 have respective operation switches on the lower support 600. Desirably, in addition to the operation switches, the lower support 600 may further include a power supply (not illustrated) supplying power to the apparatus 500 for marking the illumination area.

Figure 5:
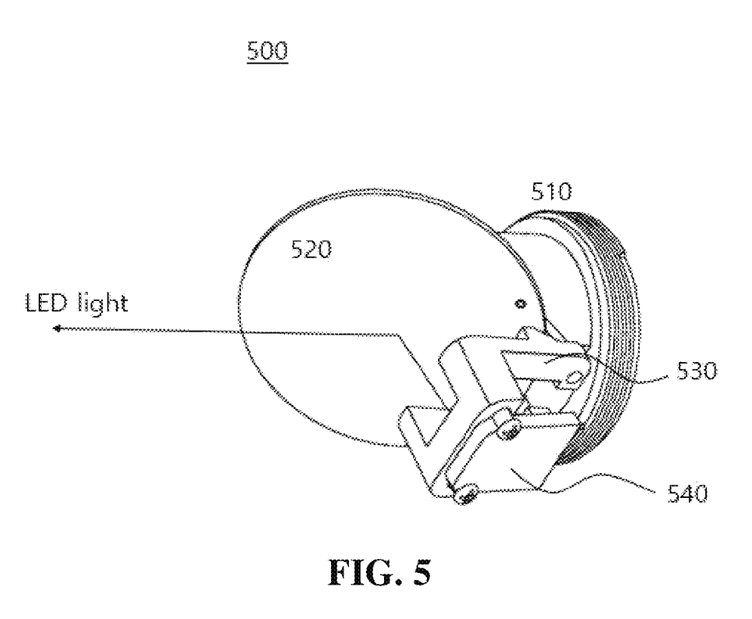
FIG. 5 is a view illustrating the apparatus for marking the irradiation area according to the embodiment of the present disclosure.
Figure 6:
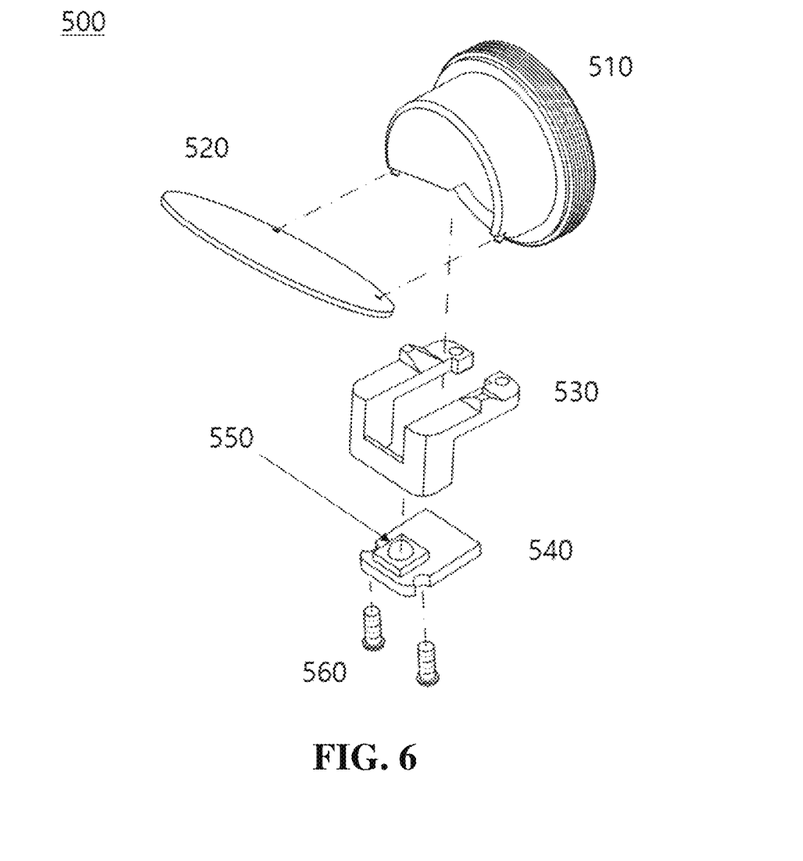
FIGS. 6 and 7 are perspective exploded views each illustrating the apparatus for marking the irradiation area according to the embodiment of the present disclosure.
Figure 7:
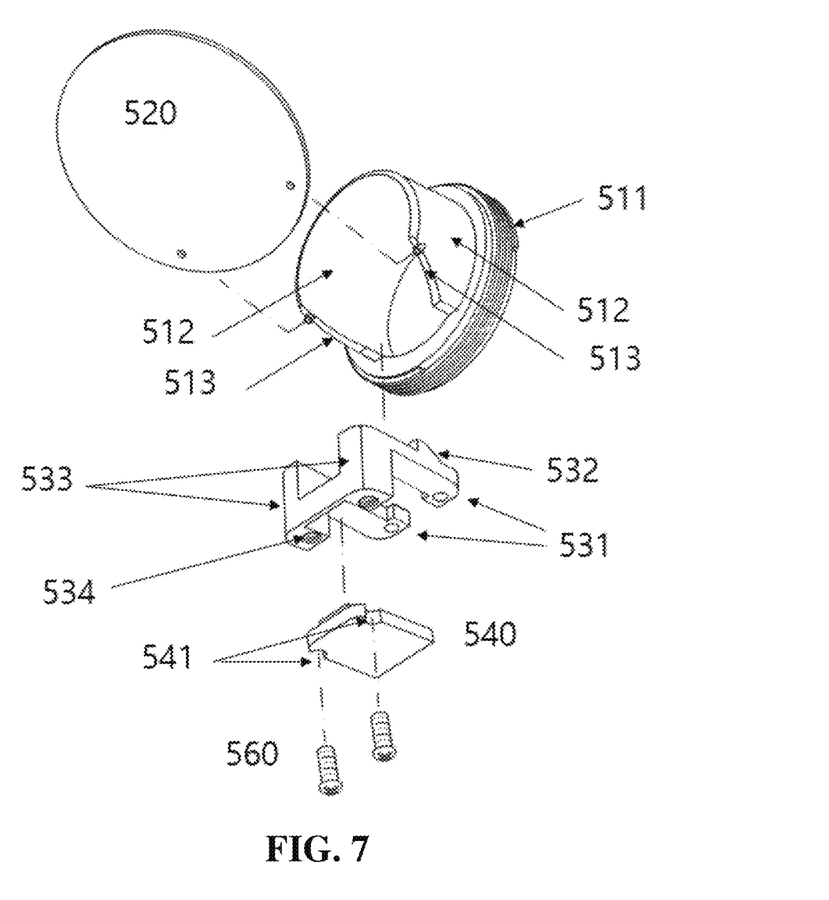

The apparatus 500 for marking the irradiation area, illustrated in FIGS. 5, 6, and 7, is configured to include a cylindrical member 510, a reflector 520, a PCB guide 530, a PCB 540, an LED light source 550, and a fastening screw 560.

The cylindrical member 510 is configured to include a connection portion 511, a hollow body member 512, and a reflector combination portion 513. The connection portion 511 is externally threaded in such a manner as to be combined with the X-ray radiation unit 300. The hollow body member 512 is provided on the connection portion 511. An inclination surface of the reflector combination portion 513, formed by obliquely cutting off a portion of the hollow body member 512 from the top thereof to close to the connection portion 511, is brought into contact with the reflector 520.

The reflector 520 is configured in such a manner that a diameter thereof is minimized to a size that allows all X-rays emitted therebehind to pass through an inclined surface of the reflector 520.

A front surface of the reflector 520 is brought into close contact with a reflector combination protrusion 532 of the PCB guide 530 that will be described below, and a rear surface thereof is brought into close contact with a combination portion 513 of the cylindrical member 510.

Light propagating from the LED light source 550 is reflected by the front surface of the reflector 520 toward the radiation tube 400.

The reflector 520 allows all X-rays emitted from the X-ray radiation unit 300 therebehind to pass through.

The PCB guide 530 is configured to include: a pair of body members 531, as guide members supporting the PCB 540, being combined in a screw-fastened manner to the reflector combination portions 513, respectively, of the cylindrical member 510, and extending lengthwise in the form of a rectangle; a pair of combination protrusions 532 protruding from upper surfaces, respectively, of the body members 531 in such a manner as to be brought into close contact with the reflector 520; a pair of PCB combination members 533 extending perpendicularly from end portions, respectively, of the body members 531 in a direction opposite to the reflector 520; and a pair of screwing grooves 534 formed in such a manner that the PCB combination member 533 and the PCB 540 are combined with the fastening screws 560, respectively, in a screw-fastened manner.

Desirably, the PCB guide 530 is formed of aluminum in such a manner as to dissipate heat.

The PCB 540 is also formed of aluminum in such a manner as to dissipate heat. For combination with the PCB 540, the LED light source 550 is bonded with the central portion of the PCB 540 using a heat conductive adhesive.

Screw fastening guidance portions 541 are further provided in such a manner as to be inward recessed from opposite lateral surfaces, respectively, of one side of the PCB 540. Thus, with the fastening screw 560, the PCB 540 and the PCB guide 530 can be combined with each other in a screw-fastened manner.

Figure 8:
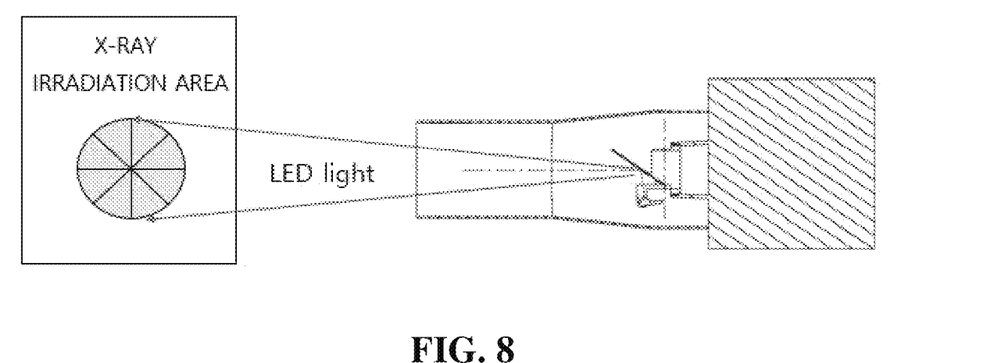
FIG. 8 is a view illustrating an example where the irradiation area for the hand-held X-ray device is marked according to the embodiment of the present disclosure.

FIG. 8 illustrates an example where the irradiation area for the hand-held X-ray device is marked according to the present disclosure.

As illustrated in FIG. 8, before performing the X-ray imaging, the user first causes the LED light source to emit the light toward the area, on which the X-ray imaging is required, of the patient to mark the irradiation area.

In a case where the center portion indicated on the irradiation area is not exactly the same as that of the area, on which the X-ray imaging is required, of the patient, even when the X-ray imaging is performed, an image sensor may not precisely capture an image of an affected area of the patient, or an opaque or bright white image may be generated due to the cone-cut phenomenon.

Therefore, with the apparatus for marking the irradiation area to the present disclosure, when the center portion of the irradiation area marked by the light emitted by the LED light source is precisely aligned with that of the affected area of the patient and then the X-ray beam is emitted, a precise clear image of the affected area of the patient can be obtained by performing the X-ray imaging.

Although the specific embodiment of the present disclosure has been described for illustrative purposes, those skilled in the art will appreciate that various modifications, additions and substitutions are possible, without departing from the scope and spirit of the disclosure as disclosed in the accompanying claims.

What is claimed is:

1. An apparatus for marking an irradiation area for a hand-held X-ray device, the device comprising an upper cover, a lower cover, an X-ray radiation unit, a radiation tube, the apparatus, and a lower support, the apparatus comprising:
   a cylindrical member;
   a reflector;
   a PCB guide;
   a PCB;
   an LED light source; and
   a fastening screw,
   wherein light emitted from the LED light source is reflected by the reflector and marks the irradiation area on a subject in front of the reflector.

2. The apparatus of claim 1, wherein the cylindrical member comprises:
   a connection portion being externally threaded in such a manner as to be combined with the X-ray radiation unit;
   a hollow body member being provided on the connection portion; and
   a reflector combination portion, with an inclination surface thereof being formed by obliquely cutting off a portion of the hollow body member from the top thereof to close to the connection portion and being brought into contact with the reflector.

3. The apparatus of claim 1, wherein a front surface of the reflector is brought into close contact with a reflector combination protrusion of the PCB guide, a rear surface thereof is brought into close contact with a combination portion of the cylindrical member, and light propagating from the LED light source is reflected by the front surface of the reflector toward the radiation tube.

4. The apparatus of claim 3, wherein the reflector is configured in such a manner that a diameter thereof is minimized to a size that allows all X-rays emitted therebehind to pass through an inclined surface 5 of the reflector.

5. The apparatus of claim 1, wherein the PCB guide comprises:
   a pair of body members, as guide members supporting the PCB, being combined in a screw-fastened manner with the reflector combination portions, respectively, and extending lengthwise in the form of a rectangle;
   a pair of combination protrusions protruding from upper surfaces, respectively, of the body members in such a manner as to be brought into close contact with the reflector;
   a pair of PCB combination members extending downward perpendicularly from end portions, respectively, of the body members in a direction opposite to the reflector; and
   a pair of screwing grooves being formed in such a manner that the PCB combination member and the PCB are combined with the fastening screws, respectively, in a screw-fastened manner.

6. The apparatus of claim 5, wherein the PCB guide is formed of aluminum.

7. The apparatus of claim 1, wherein for combination with the PCB, the LED light source is bonded with a central portion of the PCB using a heat conductive adhesive.

8. The apparatus of claim 1, further comprising: a pair of screw fastening guidance portions configured to be inward recessed from opposite lateral surfaces, respectively, of one side of the PCB.

9. The apparatus of claim 1, wherein the PCB is formed of aluminum and dissipates heat.

10. The apparatus of claim 1, wherein switches that turn on and off the LED light source and the X-ray radiation unit, respectively, are provided on the lower support.

* * * * *